US009592531B2

(12) United States Patent
Rae et al.

(10) Patent No.: US 9,592,531 B2
(45) Date of Patent: Mar. 14, 2017

(54) INK CURING APPARATUS

(71) Applicant: GEW (EC) Limited, Crawley (GB)

(72) Inventors: Malcolm Rae, Crawley (GB); James Hicks, Crawley (GB)

(73) Assignee: GEW (EC) Limited, Crawley (GB)

( * ) Notice: Subject to any disclaimer, the term of this patent is extended or adjusted under 35 U.S.C. 154(b) by 0 days.

(21) Appl. No.: 14/789,431

(22) Filed: Jul. 1, 2015

(65) Prior Publication Data

US 2016/0001321 A1 Jan. 7, 2016

(30) Foreign Application Priority Data

Jul. 1, 2014 (GB) .................................. 1411699.0

(51) Int. Cl.
*A61N 5/00* (2006.01)
*B05D 3/06* (2006.01)
*B41F 23/04* (2006.01)
*B41J 11/00* (2006.01)

(52) U.S. Cl.
CPC .......... *B05D 3/067* (2013.01); *B41F 23/0409* (2013.01); *B41F 23/0453* (2013.01); *B41J 11/002* (2013.01)

(58) Field of Classification Search
CPC ..................................................... B05D 3/067
USPC ................. 250/492.1; 362/260, 225, 217.01
See application file for complete search history.

(56) References Cited

U.S. PATENT DOCUMENTS

| | | | | |
|---|---|---|---|---|
| 3,788,560 A * | 1/1974 | Hough | B41F 23/0409 362/217.11 |
| 3,906,217 A | 9/1975 | Lackore | |
| 6,946,782 B1 | 9/2005 | Beying et al. | |
| 2005/0040341 A1* | 2/2005 | Schmitkons | F21V 19/008 250/492.1 |
| 2011/0249440 A1* | 10/2011 | Socarras | F21K 9/00 362/249.02 |
| 2012/0162976 A1* | 6/2012 | Claeys | B41F 23/0409 362/218 |

FOREIGN PATENT DOCUMENTS

| | | | |
|---|---|---|---|
| GB | 2111767 A * | 7/1983 | H01R 33/08 |
| GB | 2454789 A | 5/2009 | |
| GB | 2478717 A | 9/2011 | |
| GB | 2495355 A | 4/2013 | |

OTHER PUBLICATIONS

Search Report, GB1411699.0, dated Dec. 17, 2014, pp. 1-6.
Extended European Search Report, EP Application No. EP 15170727, dated Oct. 30, 2015, 8 pages.

* cited by examiner

*Primary Examiner* — Jason McCormack
(74) *Attorney, Agent, or Firm* — Nelson Mullins Riley & Scarborough LLP; Anthony A. Laurentano

(57) ABSTRACT

An ink curing apparatus comprising a lamp housing with a lamp fitting for a lamp terminal of a UV lamp at each opposing end, wherein at least one of the lamp fittings is non-conducting and has a non-conducting lamp terminal seat which has a concave profile for receiving a substantially spherical lamp terminal end piece; whereby, in use during the fitting or removal of a lamp, the at least one lamp fitting allows a lamp terminal end piece to rotate about multiple axes, while being retained substantially in position at the lamp fitting.

15 Claims, 4 Drawing Sheets

INK CURING APPARATUS

CROSS REFERENCE TO RELATED APPLICATIONS

This application is based upon and claims the benefit of priority from GB1411699.0 filed on Jul. 1, 2014, the contents of which are incorporated herein by reference.

BACKGROUND OF THE INVENTION

The present invention relates to a UV lamp. More specifically, the invention relates to a UV lamp for use with ink curing apparatus used commonly in the printing industry.

Lamps used in ink curing apparatus generally comprise a glass tube with an electrode extending into each end of the lamp tube. It is common for the terminal assembly at each end of the tube to be pinch sealed and received within a small ceramic block into which the free end of each electrode also extends. A wire extends out of the ceramic block for connection to the electricity supply used to power the lamp. Existing lamp terminal arrangements are connected to the ink curing apparatus using a threaded screw clamped with a nut. The applicant's earlier UK patent application no. GB1004255.4 discloses a simplified lamp terminal arrangement having a male/female connection means at each end of the lamp.

UV lamps for use in ink curing machines are run at high intensities and consequently have a limited life span such that lamps have to be frequently cleaned and changed. The length of the lamp and the possibility of marking or breaking the glass tube mean that it is important for care to be taken when inserting a lamp into the apparatus. Existing lamps require a first end of the lamp to be inserted before a second end of the lamp is inserted to enable both ends of the lamp to be secured to the ink curing apparatus. Manoeuvring both ends of the lamp in this way often makes maintenance and repair difficult for a single person to complete; that is, safely inserting the lamp into the housing often requires two people. It has been found that manoeuvring the second end of the lamp to connect the lamp causes the first end of the lamp to be displaced from its desired position. There is a significant risk that this displacement of the first end of the lamp can cause the first lamp end to snap from the glass tube or be otherwise damaged whilst a user is endeavouring to connect the second end of the lamp.

SUMMARY OF THE INVENTION

The present invention seeks to alleviate the aforementioned disadvantages with known UV lamps by providing an improved ink curing apparatus that allows a UV lamp to be conveniently and safely changed, whilst reducing the time and cost of maintenance of the UV curing apparatus.

In one aspect of the present invention there is provided an ink curing apparatus comprising:

a lamp housing with a lamp fitting for a lamp terminal of a UV lamp at each opposing end;

wherein at least one of the lamp fittings is non-conducting and has a non-conducting lamp terminal seat, which has a concave profile for receiving a substantially spherical lamp terminal end piece;

whereby, in use during the fitting or removal of a lamp, the at least one lamp fitting allows a lamp terminal end piece to rotate about multiple axes, whilst being retained substantially in position at the lamp fitting.

The present invention allows for a lamp to be fitted and replaced by a single user, because the first end of the lamp is held in position whilst connection is made at the second end of the lamp. The first end of the lamp is not rigidly held to allow the second end of the lamp to be manoeuvred into position. Maintenance of the improved UV curing apparatus is safer, quicker and more convenient, whilst reducing maintenance costs and safeguarding against accidental damage to the lamp. The "lamp terminal" is understood to comprise all components at the end of the lamp, including the electrical connector. It is also understood that "restricted movement" refers to limited movement over a receiving surface, where the lamp terminal will ultimately be fixed.

The end pieces of the lamp housing of the present invention have a profile, which is preferably substantially spherical. Thus, together with the concave configuration of the lamp fitting allows the lamp to be easily manoeuvred through multiple degrees of freedom; for example the permitted movement at the or each lamp end is akin to that of a ball and socket joint. The present invention allows for installation and removal of a lamp safely and quickly by a single user because there is no axial constraint. The present invention mitigates the risk of the lamp being damaged when fitting or removing the lamp from the housing.

Preferably, the or each lamp fitting is made of a ceramic or similar insulating material.

An insulating material prevents the risk of electrical tracking or short circuits between the lamp fitting and the aluminium lamp housing.

Preferably, the or each lamp fitting is a two-part device comprising a lamp terminal seat and a closure means.

By providing a lamp terminal seat and a closure means, the electrical tracking distance between the lamp terminal and the conducting lamp housing is increased to prevent electrical tracking and short circuiting.

Preferably, the lamp terminal seat is curved.

Preferably, the lamp terminal seat is U-shaped.

A curved, U-shaped lamp terminal seat allows for a complementary-shaped lamp terminal to smoothly roll over the seat, and move in all degrees of freedom, around the lamp fitting.

In a second aspect, the present invention provides a UV lamp for an ink curing apparatus, the lamp having a lamp terminal with at least one non-conducting end piece, wherein the non-conducting end piece is substantially spherical.

Preferably, the or each curved end piece is made of ceramic or similar insulating material.

A curved or substantially spherical lamp end piece rolls easily over a complementary curved lamp terminal seat to allow a user to easily manoeuvre the lamp into position. The shape of the end piece allows the lamp to be easily manoeuvred through multiple degrees of freedom; for example the permitted movement at the or each lamp end is akin to that of a ball and socket joint. The present invention allows for installation and removal of a lamp safely and quickly by a single user because there is no axial constraint and mitigates the risk of the lamp being damaged when fitting or removing the lamp from the housing.

BRIEF DESCRIPTION OF THE DRAWINGS

One embodiment of the present invention will now be described, by way of example with reference to the accompanying drawings, in which.

DETAILED DESCRIPTION

Figure 1A:
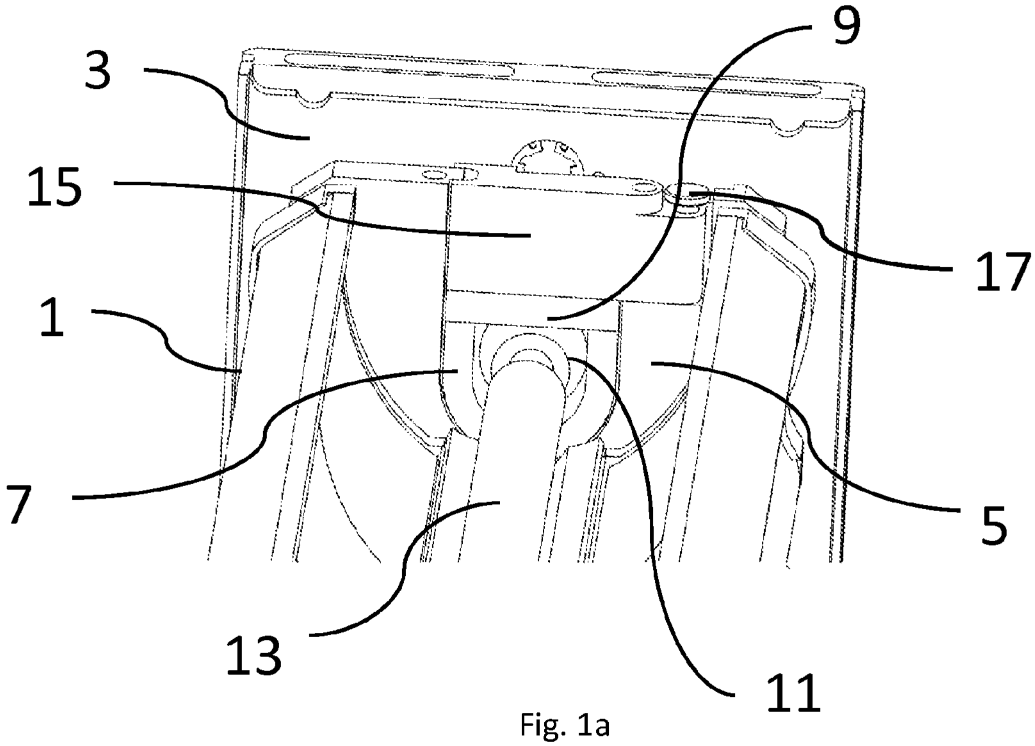
FIG. 1*a* is a perspective view of one end of a lamp housing for an ink curing apparatus in accordance with the present invention, showing the lamp fitting with a UV lamp fitted thereto.

Referring to FIG. 1*a*, the ink curing apparatus comprises a lamp housing 1, which is an interchangeable "cassette" 3 for use in ultra violet (UV) print curing. Each end of the lamp housing 1 has an aluminium end plate 5. A second endplate at the opposing end of the lamp housing 1 is not shown in FIG. 1. The cassette 3 comprises a lamp fitting 7, 9 having a curved ceramic body 7 fixed to the cassette 3 and a removable ceramic closure member 9 between which an opening 11 is defined. The cassette 3 is provided with a connection means (not shown) for connecting and disconnecting a UV lamp 13 to and from the power connected to the housing 1. For example, the connection means is a plug/socket arrangement allowing a lamp 13 to be connected into cassette 3 using a "push-fit" connection. The lamp 13 has a rod-shaped, hollow main body made, for example, of quartz. The main body has located therein chemical compounds to provide ultra violet (UV) radiation when an electrical source is applied to the lamp 13.

As shown in FIG. 1*a* the cassette 3 also comprises a pivotable lamp door 15, which is hinged about a knurled screw 17. The configuration of the lamp door 15 ensures that, when both ends of the lamp 13 are connected to their respective push fit connections, and the lamp door 15 is closed, the lamp 13 is retained so that it cannot fall out in any orientation.

Figure 1B:
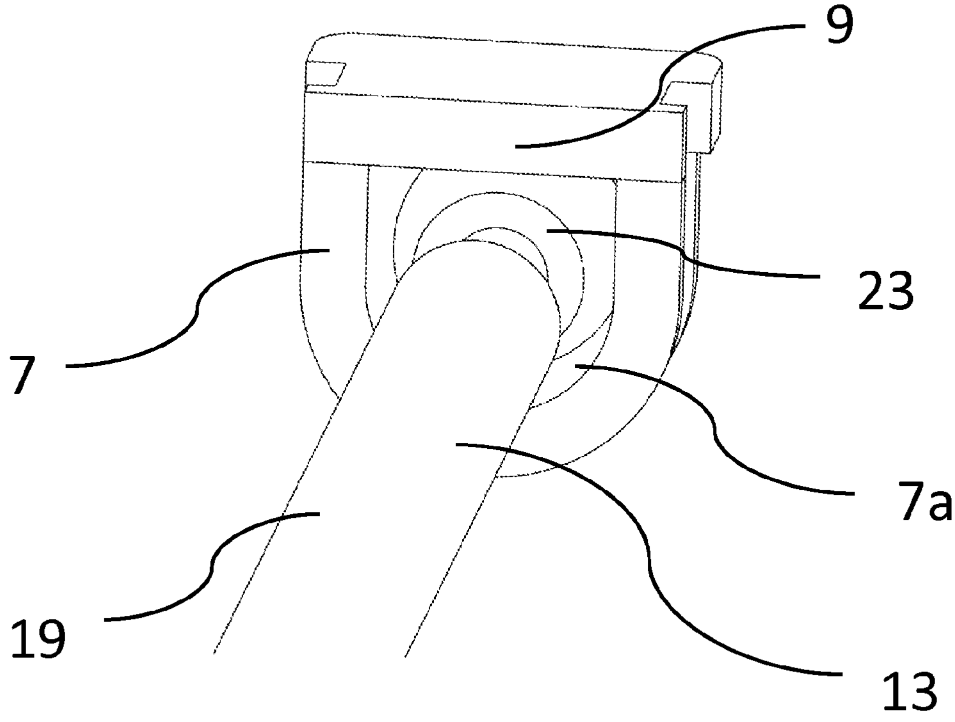
FIG. 1*b* is an enlarged perspective view of the lamp fitting showing a UV lamp fitted therethrough.
Figure 2A:
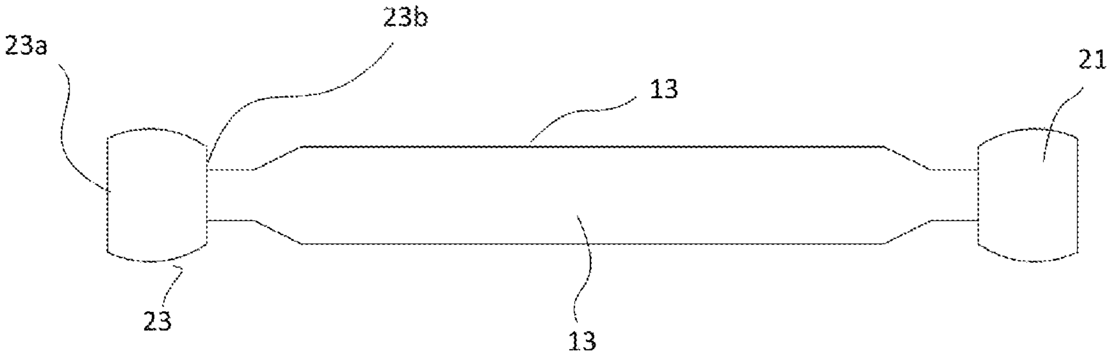
FIG. 2*a* is a cross-sectional view through a UV lamp constructed in accordance with a second aspect of the present invention.

Referring to FIGS. 1*b* and 2*a*, a UV lamp 13 comprises a lamp terminal assembly 21 at each of its ends. The assembly 21 comprises a curved ceramic block 23, having a substantially circular cross-section. The ceramic block 23 is a lamp terminal end piece, which has an outer surface, which is substantially spherical. The sphere is truncated to provide two opposing flat surfaces 23*a*, 23*b*. That is, the ceramic block 23 of the lamp terminal end piece is a sphere having a segment cap cut off by planar surfaces 23*a*, 23*b*. The ceramic block 23 of the lamp terminal end piece has a cylindrical hollow passing through it into which the lamp 13 is fixed. An electrode (not shown) passes into the glass tube 19 of the lamp 13 and into the curved ceramic block 23. The ceramic block 23 at each end of the lamp 13 provides for ease of insertion and removal of the lamp 13 into and from the end plate 5 and curved ceramic body 7.

Figure 2B:
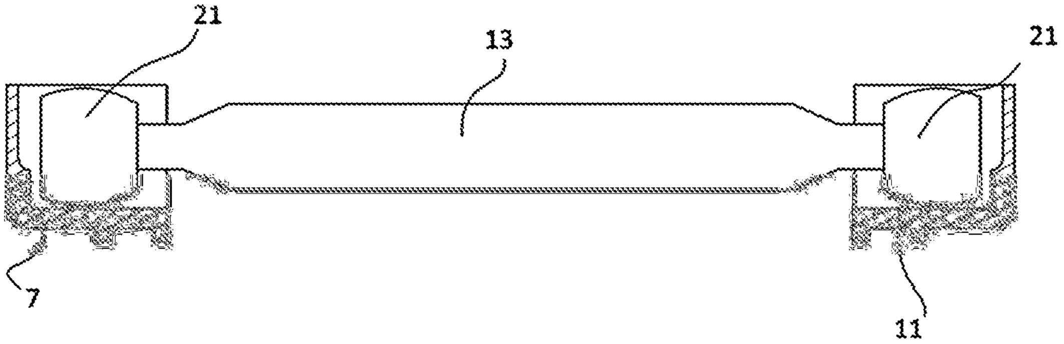
FIG. 2*b* is a cross-sectional view through the UV lamp of FIG. 2*a*, showing a UV lamp fitted to a lamp fitting.

Referring to FIG. 1*b* and FIG. 2*b*, the diameter at the widest point of the curved ceramic block 23 is about 1 mm less than the greatest width of the opening 11 provided by the curved ceramic body 7.

Referring to FIGS. 1*b*, 3*a*, 3*b* and 3*c*, in use, the curved ceramic block 23 of a first end of the lamp 13 is placed on the curved receiving face 7*a* of the ceramic body 7, which acts as a terminal seat. The ceramic closure member 9 of the cassette 3 is closed i.e. placed over the ceramic body 7 to restrict the movement of the first end of the lamp 13. The ceramic block 23 of the lamp terminal 21 rolls over the curved face 7*a* of the ceramic body 7, so that the lamp 13 is moveable about multiple axis in all degrees of freedom, whilst still being held, i.e. substantially retained, within the lamp end ceramic fitting 7, 9; i.e. so that movement is restricted.

Figure 3A:
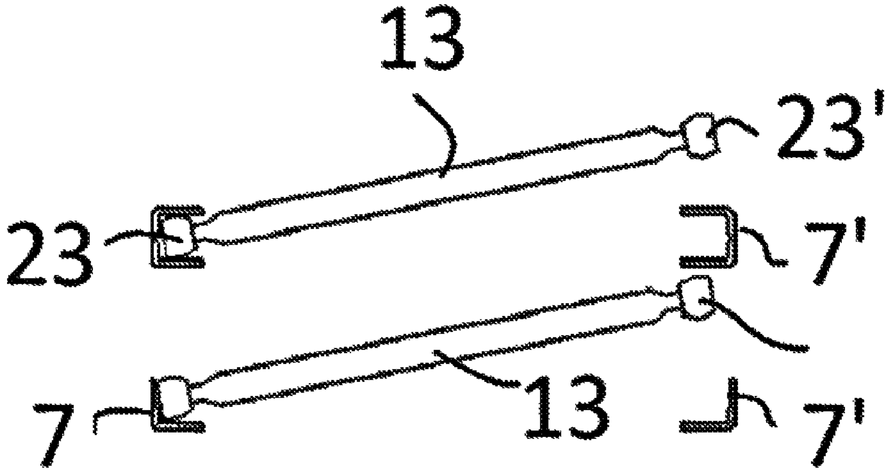
FIGS. 3*a*, 3*b* and 3*c* are top and side schematic views showing the process of fitting a UV lamp to the lamp fittings of a lamp housing.

As shown in FIG. 3*a*, a first end of the lamp 13 is placed on the curved face 7*a* of the ceramic body 7 with the ceramic closure member 9 placed over the ceramic body 7 at the lamp end so that movement of the lamp 13 is restricted. To manoeuvre the second end of the lamp 13 into the second ceramic body 7, the ceramic block 23' of the lamp terminal is moved over the ceramic block 7 so that the lamp 13 can be fitted whilst the lamp 13 is out of line, thus reducing the possibility of snapping the lamp end 11.

Figure 3B:
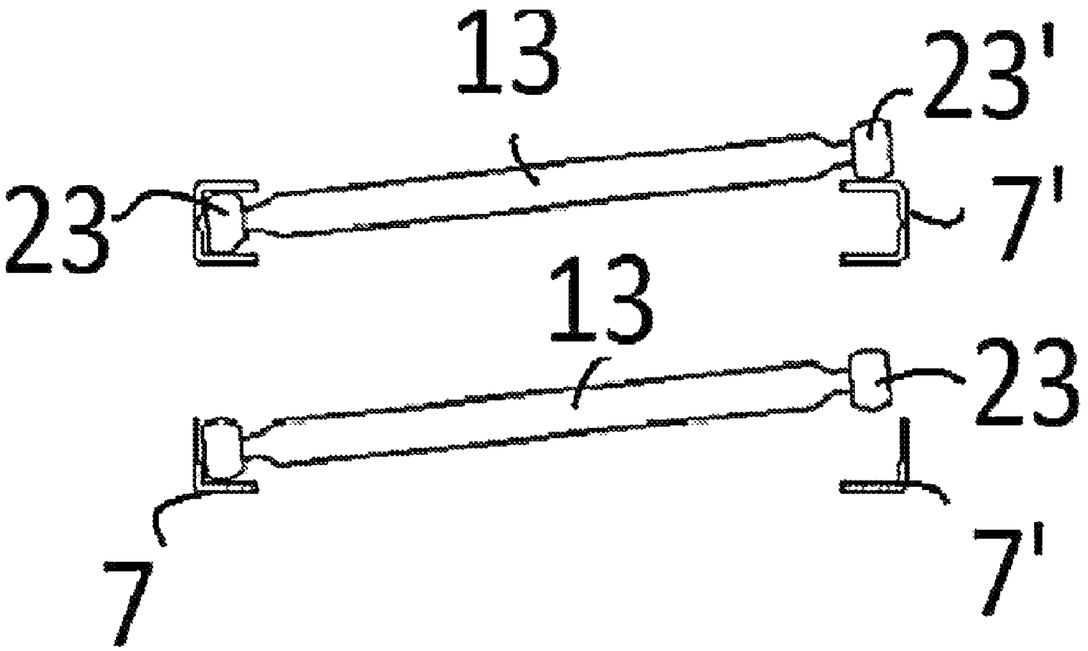

As shown in FIGS. 1*b* and 3*b*, with the first end of the lamp in position, the configuration of the lamp fitting 7 allows for movement of the lamp 13 in all degrees of freedom, but restricts movement of the first lamp terminal 21 out of the fitting, which comprises ceramic body 7 and closure member 9. The fitting prevents the first end of the lamp 13 disengaging with the fitting 7. The curved ceramic face 7*a* of the lamp fitting allows the lamp end piece 23 to rotate about multiple axis; i.e. it can be manoeuvred through multiple degrees of freedom. This allows the ceramic block 23' at the other, i.e. second, end of the lamp 13 to be positioned into the respective ceramic fitting, which comprises a ceramic body 7' and closure member (not shown), without any risk of damage to the first end of the lamp 13.

Figure 3C:
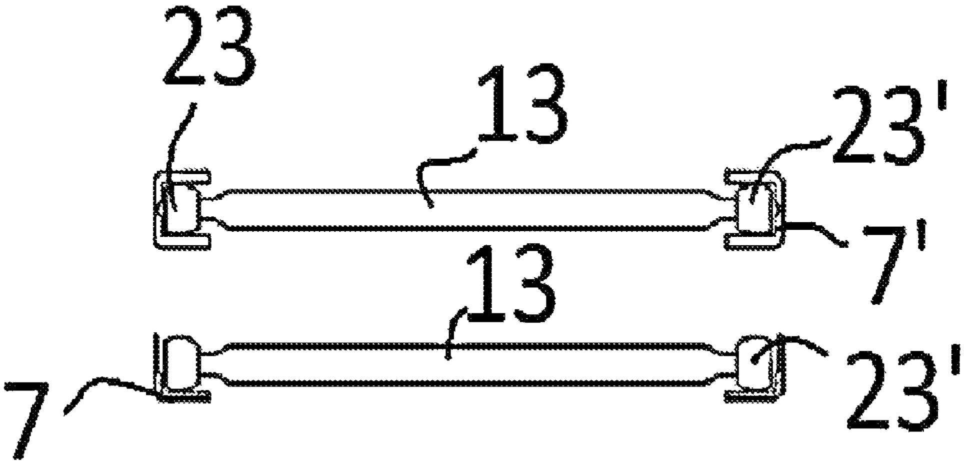

Referring to FIG. 3*c* and FIG. 1*a*, with both ends of the lamp 13 in position, i.e. fitted on the lamp fitting 7, 7' within the cassette 3, the second ceramic closure member is inserted to meet the curved ceramic body 7'. The lamp door 15 is pivoted and closed, to retain the lamp 13 in place for UV print curing to commence.

In use, the distance between the lamp's electrical connection, i.e. between the assembly 21 and the aluminium end plate 5 of the cassette 3 is sufficient to ensure that the electrical connection is insulated by the ceramic components 7, 7', 9, 23 described above. This significantly decreases any risk of electrical tracking or short circuiting between the lamp's electrical connection and the end plate 5.

When the lamp 13 is spent, the connection to the cassette 3 and the lamp 13 is disconnected. The lamp door 15 at each end of the lamp cassette 3 is opened; the ceramic closure member 9 is removed and a first end of the lamp 13 is removed from the curved ceramic body 7. During removal of the first lamp end, the second end of the lamp 13 is moveable in all degrees of freedom, whilst still be held within the ceramic fitting 7', 9. The curved ceramic body of the lamp fitting is allowed to rotate about multiple axis and so has multiple degrees of freedom. Following removal of the first lamp terminal 21, the second lamp terminal 21' is also removed from the respective ceramic fitting and so from the cassette 3.

It will be appreciated that the foregoing is merely exemplary of the lamp and lamp housing of the present invention. The skilled reader will understand that modifications can readily be made thereto without departing from the true scope of the present invention as defined by the claims.

The invention claimed is:

1. An ink curing apparatus comprising:

a lamp housing with a lamp fitting at each opposing end;

a lamp having at least one substantially spherical terminal end piece;

wherein at least one of the lamp fittings is non-conducting and has a non-conducting lamp terminal seat, which has a concave profile for receiving the substantially spherical lamp terminal end piece;

whereby, in use during the fitting or removal of the lamp, the at least one lamp fitting allows the lamp terminal end piece to rotate about multiple axes, whilst being retained substantially in position at the lamp fitting.

2. An ink curing apparatus according to claim 1 wherein the or each lamp fitting is made of a ceramic material.

3. An ink curing apparatus according to claim 1 wherein the or each lamp fitting is a two-part device comprising the lamp terminal seat and a closure means.

4. An ink curing apparatus according to claim 1 wherein the lamp terminal seat is curved.

5. An ink curing apparatus according to claim 1 wherein the lamp-terminal seat is U-shaped.

6. A UV lamp for an ink curing apparatus, the lamp having a lamp terminal with at least one non-conducting end piece, wherein the non-conducting end piece is substantially spherical.

7. A UV lamp for an ink curing apparatus according to claim 6 wherein the or each non-conducting end piece is made of ceramic.

8. A UV lamp according to claim 6 wherein the non-conducting end piece is a truncated sphere.

9. A UV lamp according to claim 6 wherein the non-conducting end piece is formed of a substantially spherical ceramic block truncated to provide two opposing flat surfaces.

10. An ink curing apparatus according to claim 1 wherein the terminal end piece is a truncated sphere.

11. An ink curing apparatus according to claim 1 wherein the terminal end piece is formed of a substantially spherical ceramic block truncated to provide two opposing flat surfaces.

12. An ink curing apparatus comprising:

a lamp housing with a lamp fitting for a lamp terminal of a UV lamp at each opposing end;

wherein at least one of the lamp fittings is non-conducting and has a non-conducting lamp terminal seat, which has a concave profile for receiving a substantially spherical lamp terminal end piece;

wherein the or each lamp fitting is a two-part device comprising a lamp terminal seat and a closure means closable to prevent removal of a lamp terminal end piece provided in the fitting;

whereby, in use during the fitting or removal of the lamp, the at least one lamp fitting allows the lamp terminal end piece to rotate about multiple axes, whilst being retained substantially in position at the lamp fitting, and being prevented from disengaging from the lamp fitting.

13. An ink curing apparatus according to claim 12 wherein the or each lamp fitting is made of a ceramic material.

14. An ink curing apparatus according to claim 12 wherein the lamp terminal seat is curved.

15. An ink curing apparatus according to claim 12 wherein the lamp-terminal seat is U-shaped.

* * * * *